(12) United States Patent
Mangual-Soto

(10) Patent No.: US 12,011,600 B2
(45) Date of Patent: *Jun. 18, 2024

(54) SYSTEM FOR ADJUSTING VENTRICULAR REFRACTORY PERIODS

(71) Applicant: Pacesetter, Inc., Sylmar, CA (US)

(72) Inventor: Jan O. Mangual-Soto, Rho (IT)

(73) Assignee: Pacesetter, Inc., Sylmar (CA)

( * ) Notice: Subject to any disclaimer, the term of this patent is extended or adjusted under 35 U.S.C. 154(b) by 197 days.

This patent is subject to a terminal disclaimer.

(21) Appl. No.: 17/725,599

(22) Filed: Apr. 21, 2022

(65) Prior Publication Data

US 2022/0241597 A1 Aug. 4, 2022

Related U.S. Application Data

(63) Continuation of application No. 16/895,500, filed on Jun. 8, 2020, now Pat. No. 11,338,146.

(51) Int. Cl.
*A61N 1/368* (2006.01)
*A61N 1/37* (2006.01)

(52) U.S. Cl.
CPC ........... *A61N 1/3702* (2013.01); *A61N 1/368* (2013.01); *A61N 1/3682* (2013.01); *A61N 1/3684* (2013.01); *A61N 1/3686* (2013.01); *A61N 1/3706* (2013.01); *A61N 1/36842* (2017.08); *A61N 1/36843* (2017.08)

(58) Field of Classification Search
CPC .... A61N 1/368; A61N 1/3682; A61N 1/3684; A61N 1/36842; A61N 1/36843
See application file for complete search history.

(56) References Cited

U.S. PATENT DOCUMENTS

2019/0046802 A1 2/2019 Min et al.

*Primary Examiner* — Brian T Gedeon
(74) *Attorney, Agent, or Firm* — Dean D. Small; The Small Patent Law Group, LLC

(57) ABSTRACT

A system is provided for controlling a left univentricular (LUV) pacing therapy using an implantable medical device (IMD). The system also includes one or more processors configured to determine an atrial-ventricular (AV) conduction interval ($AR_{RV}$) between the A site and a first RV sensed event at the RV site, determine an inter-ventricular (VV) conduction interval ($R_{LV}\text{-}R_{RV}$) between a paced event at the LV site and a second RV sensed event at the RV site, and set a ventricular refractory period (VRP) based on at least one of the AV conduction interval or the VV conduction interval and a predetermined offset. The one or more processors are also configured to blank signals over the RV sensing channel during the VRP.

20 Claims, 6 Drawing Sheets

SYSTEM FOR ADJUSTING VENTRICULAR REFRACTORY PERIODS

REFERENCE TO RELATED APPLICATIONS

The present application is a continuation application of, and claims priority to, U.S. application Ser. No. 16/895,500, Titled "SYSTEM FOR ADJUSTING VENTRICULAR REFRACTORY PERIODS" which was filed on Jun. 8, 2020, the complete subject matter of which is expressly incorporated herein by reference in its entirety.

BACKGROUND

Embodiments herein generally relate to a system and method for adjusting ventricular refractory periods during left ventricle only pacing.

Most conventional pacing algorithms call for pacing in the right ventricle (RV) alone or in combination with left ventricular (LV) pacing. However, certain patients may exhibit circumstances where RV pacing may not be necessary.

To this end, LV lead design and device algorithms have improved patient outcomes during cardiac resynchronization therapy (CPT). LV only pacing has been shown to be as efficient at conventional biventricular pacing in patients with wide QRS duration, intact atrioventricular (AV) conduction and left bundle branch block (LBBB).

However, LV only pacing can result in ventricle oversensing, or double-counting, of ventricle events in the right ventricle lead (RV), i.e. intrinsic or LV pacing wave front. Additionally, LV only pacing can also lead to ventricle oversensing if the ventricle refractory window is too short.

BRIEF SUMMARY

In accordance with embodiments herein, a system is provided for controlling a left univentricular (LUV) pacing therapy using an implantable medical device (IMD). The system includes electrodes configured to be located proximate to an atrial (A) site, a left ventricular (LV) site and a right ventricular (RV) site of the heart, a sensing circuitry configured to define an atrial sensing channel and an RV sensing channel, and a memory to store program instructions. The system also includes one or more processors configured to implement the program instructions to determine an atrial-ventricular (AV) conduction interval ($AR_{RV}$) between the A site and a first RV sensed event at the RV site, determine an inter-ventricular (VV) conduction interval ($R_{LV}$-$R_{RV}$) between a paced event at the LV site and a second RV sensed event at the RV site, and set a ventricular refractory period (VRP) based on at least one of the AV conduction interval or the VV conduction interval and a predetermined offset. The one or more processors are also configured to blank signals over the RV sensing channel during the VRP, and manage the LUV pacing therapy based on the signals sensed over the RV sensing channel outside of the VRP, wherein the LUV pacing therapy lacks pacing in the RV.

Optionally, the LUV pacing therapy is not based on signals sensed in the LV. In another aspect, the one or more processors also deliver an A paced event at the A site, obtain cardiac activity (CA) signals over the RV sensing channel, and identify the first RV sensed event from the CA signals obtained over the RV sensing channel, the AV conduction interval determined based on a time between the A paced event and the first RV sensed event. In another aspect, the one or more processors also deliver an LV paced event at the LV site, obtain cardiac activity (CA) signals over the RV sensing channel, and identify the second RV sensed event from the CA signals obtained over the RV sensing channel, the VV conduction interval determined based on the time between the LV paced event and the second RV sensed event.

Optionally, the sensing circuitry does not obtain signals at the LV site. In one aspect the one or more processors identify a longer one of the AV conduction interval and the VV conduction interval, the VRP set based on the longer one of the AV and VV conduction intervals. In another aspect, the VRP defines a blanking interval during which signals, that occur over the RV sensing channel, are ignored.

In one or more embodiments, a computer implemented method for controlling a left univentricular (LUV) pacing therapy using an implantable medical device (IMD) is provided. The method includes determining an atrial-ventricular (AV) conduction interval ($AR_{RV}$) between an atrial (A) site and a first right ventricular (RV) sensed event at a RV site, determining an inter-ventricular (VV) conduction interval ($R_{LV}$-$R_{RV}$) between a paced event at a left ventricular (LV) site and a second RV sensed event at the RV site, and setting a ventricular refractory period (VRP) based on at least one of the AV conduction interval or the VV conduction interval and a predetermined offset. The method may also include blanking signals over a RV sensing channel during the VRP, and managing the LUV pacing therapy based on the signals sensed over the RV sensing channel outside of the VRP, wherein the LUV pacing therapy lacks pacing in the RV.

Optionally, the LUV pacing therapy is not based on signals sensed in the LV. In another aspect the method also includes delivering an A paced event at the A site, obtaining cardiac activity (CA) signals over the RV sensing channel, and identifying the first RV sensed event from the CA signals obtained over the RV sensing channel, the AV conduction interval determined based on a time between the A paced event and the first RV sensed event. In another aspect, the method also includes delivering an LV paced event at the LV site, obtaining cardiac activity (CA) signals over the RV sensing channel and identifying the second RV sensed event from the CA signals obtained over the RV sensing channel, the VV conduction interval determined based on the time between the LV paced event and the second RV sensed event.

Optionally, the sensing circuitry does not obtain signals at the LV site. In one aspect, the method also includes identifying a longer one of the AV conduction interval and the VV conduction interval, the VRP set based on the longer one of the AV and VV conduction intervals. In another aspect, the VRP defines a blanking interval during which signals, that occur over the RV sensing channel, are ignored.

In one or more embodiments, a system for controlling a left univentricular (LUV) pacing therapy using an implantable medical device (IMD) is provided. The system includes electrodes configured to be located proximate to an atrial (A) site, a left ventricular (LV) site and a right ventricular (RV) site of the heart; sensing circuitry configured to define an atrial sensing channel and an RV sensing channel, and memory to store program instructions. The system also includes one or more processors configured to implement the program instructions to determine an atrial-ventricular (AV) conduction interval ($AR_{RV}$) between the A site and a first RV sensed event at the RV site, determine an inter-ventricular (VV) conduction interval ($R_{LV}$-$R_{RV}$) between a paced event at the LV site and a second RV sensed event at the RV site, and set a ventricular refractory period (VRP) based on at least one of the AV conduction interval or the VV conduction interval and a predetermined offset. The one or more processors are also configured to blank signals over the RV sensing channel during the VRP, manage the LUV pacing therapy based on the signals sensed over the RV sensing channel outside of the VRP, wherein the LUV pacing therapy lacks pacing in the RV, and identify a longer one of the AV conduction interval and the VV conduction interval, the VRP set based on the longer one of the AV and VV conduction interval. The VRP defines a blanking interval during which signals, that occur over the RV sensing channel, are ignored.

Optionally, the LUV pacing therapy is not based on signals sensed in the LV. In one aspect the one or more processors also deliver an A paced event at the A site, obtain cardiac activity (CA) signals over the RV sensing channel, and identify the first RV sensed event from the CA signals obtained over the RV sensing channel, the AV conduction interval determined based on a time between the A paced event and the first RV sensed event. In one aspect, the one or more processors also deliver an LV paced event at the LV site, obtain cardiac activity (CA) signals over the RV sensing channel and identifying the second RV sensed event from the CA signals obtained over the RV sensing channel, the VV conduction interval determined based on the time between the LV paced event and the second RV sensed event. In another aspect, the sensing circuitry does not obtain signals at the LV site. In one example, the one or more processors also determine the first RV sensed event is not a premature ventricular contraction (PVC); and counting the first RV sensed event.

DETAILED DESCRIPTION

Figure 1:
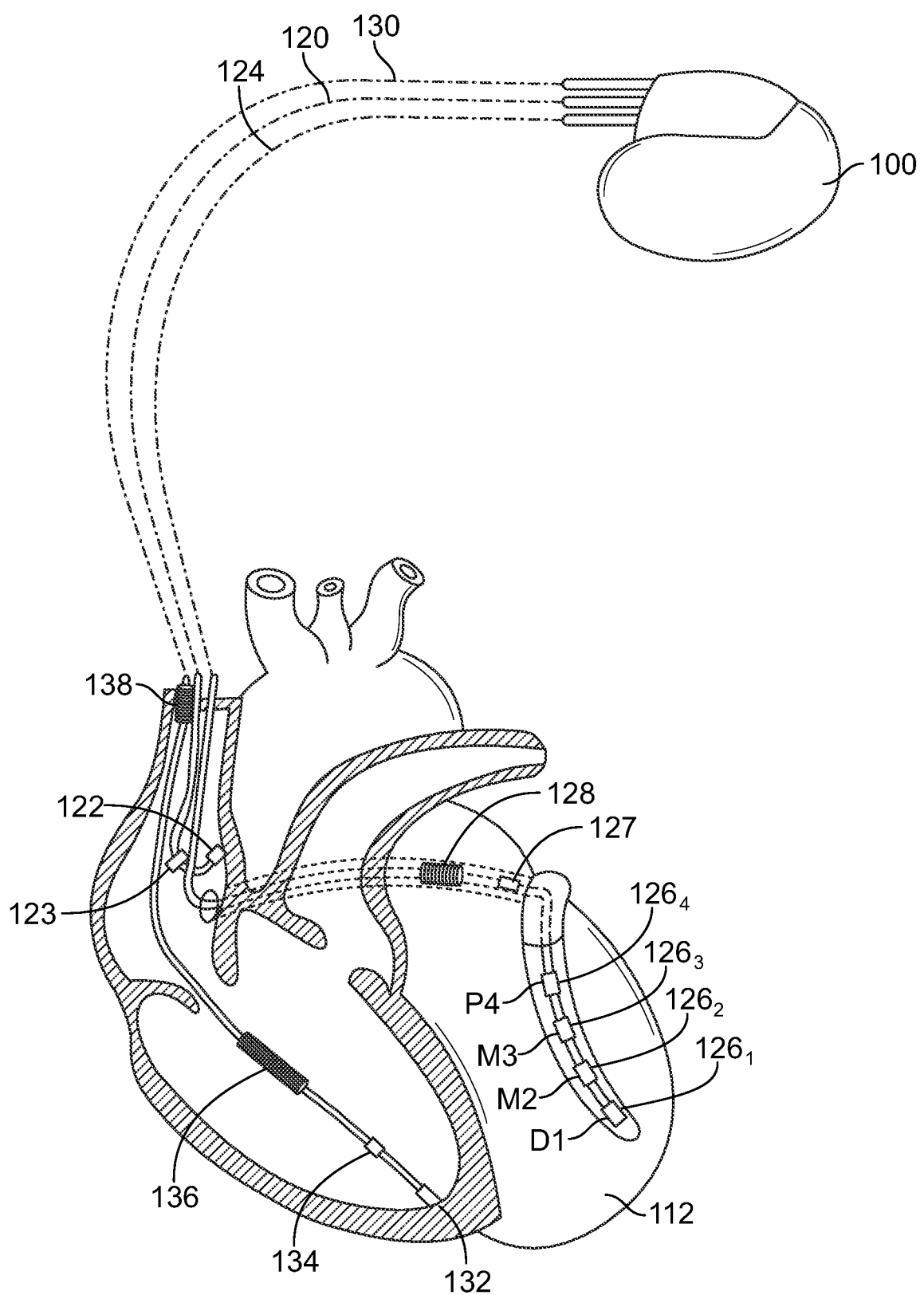
FIG. 1 illustrates an exemplary IMD formed in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The system and methods described herein are provided to avoid RV lead oversensing by adjusting the ventricular refractory period based on the right atrial (RA) and LV to RV sensed delays. In particular, the delay from LV paced to the RV sensed are measured (LVp-RVs) at the shortest possible paced/sensed AV delay to ensure sensing in the RV is due to LV pacing wave front, where the measurement is LVp-RVs. The delay from the RA paced and RA sensed is measured to the RV with no LV pacing, where the measurement is RAp/RAs-RVs. The ventricle refractory period (VRP) is programmed to Xms longer than the largest measurement between RAp/RAs-RVs and LVp-RVs. A RVs counter is initialized to 0. The system then continuously records if a ventricle sensed event is detected just outside of the VRP. If an event is sensed, first it is verified if the origin is a premature ventricular contraction (PVC). If so, monitoring continues. If not, then a RVs counter is increased by 1 (RVs=RVs+1). When the RVs counter reaches a threshold, or maximum of sensed beats, the delays (LVp-RVs and RAp/RAs-RVs) are measured again and the VRP is updated.

The terms "beat", and "event" are used interchangeably and refer to both normal and/or abnormal events.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/ arrhythmic. Non-limiting examples of CA signals include ECG signals obtained by cutaneous electrodes, and EGM signals obtained by subcutaneous electrodes.

The term "delay" shall refer to a parameter programmed or set in connection with the operation of the IMD. For example, an IMD may have a programmed AV delay, post ventricular atrial refractory period (PVARP) delay, and the like.

The term "ignored" shall mean to intentionally disregard. In examples, intentionally disregarding a sensed event can be accomplished by not monitoring an event, not sensing an event, not communicating a sensed event, not using information associated with a sensed event in an analysis, algorithm, function, equation, etc., eliminating or not using analysis made with a sensed event, or the like. In each example, the event sensed is considered a blanked event sensed, or ignored through blanking or a blanking signal.

The term "IMD" shall mean an implantable medical device. Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, U.S. application Ser. No. 15/672,178, entitled "METHOD AND DEVICE FOR CONTROLLING LEFT VENTRICULAR PACING THERAPY", filed Aug. 8, 2017, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support, and/or merely monitor one or more physiologic characteristics of interest (e.g., PAP, CA signals, impedance, heart sounds).

The term "interval" shall refer to an intrinsic characteristic of an anatomy. For example, a heart exhibits an intrinsic AV conduction interval, VV conduction interval and the like.

The terms "left univentricular pacing", "LUV pacing" and "left ventricular only pacing" are used interchangeably to refer to pacing therapies that deliver pacing stimulation at one or more left ventricular (LV) sites and do not deliver any pacing stimulation to any right ventricular (RV) sites. The terms "left univentricular pacing", "LUV" and "left ventricular only pacing" include therapies that deliver atrial pacing, but do not include biventricular pacing therapies.

The term "non-pacing/sensing electrode" refers to an electrode that is controlled and utilized only for sensing operations. The non-pacing-sensing electrode may be on a lead coupled to a lead-based implantable medical device and/or external programmer to perform sensing of cardiac signals at the corresponding site, and is not controlled or utilized to deliver pacing pulses. The non-pacing-sensing electrode may be on a leadless implantable medical device that uses the electrode to perform sensing of cardiac signals at the corresponding site, and does not use the electrode to deliver pacing pulses.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the ICM and a local external device, and/or iii) receiving the data, signals, information, etc. at a remote server over a network connection. The obtaining operation, when from the perspective of an ICM, may include sensing new signals in real time, and/or accessing memory to read stored data, signals, information, etc. from memory within the ICM. The obtaining operation, when from the perspective of a local external device, includes receiving the data, signals, information, etc. at a transceiver of the local external device where the data, signals, information, etc. are communicated from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The term "pacing/sensing electrode" refers to an electrode that is controlled and utilized by an implantable medical device and/or external programmer to perform both delivery of pacing pulses at a site and sensing of cardiac signals at the same site.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The phrase "wherein the LUV pacing therapy is not based on signals sensed in the LV" shall mean that left univentricular pacing is provided based on signals sensed in an area of the heart other than the LV. The sensing instead may occur in the A, and/or RV, but no the LV.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals, and delivering stimulation in the form of pacing and shock therapy to the right ventricle.

Figure 2:
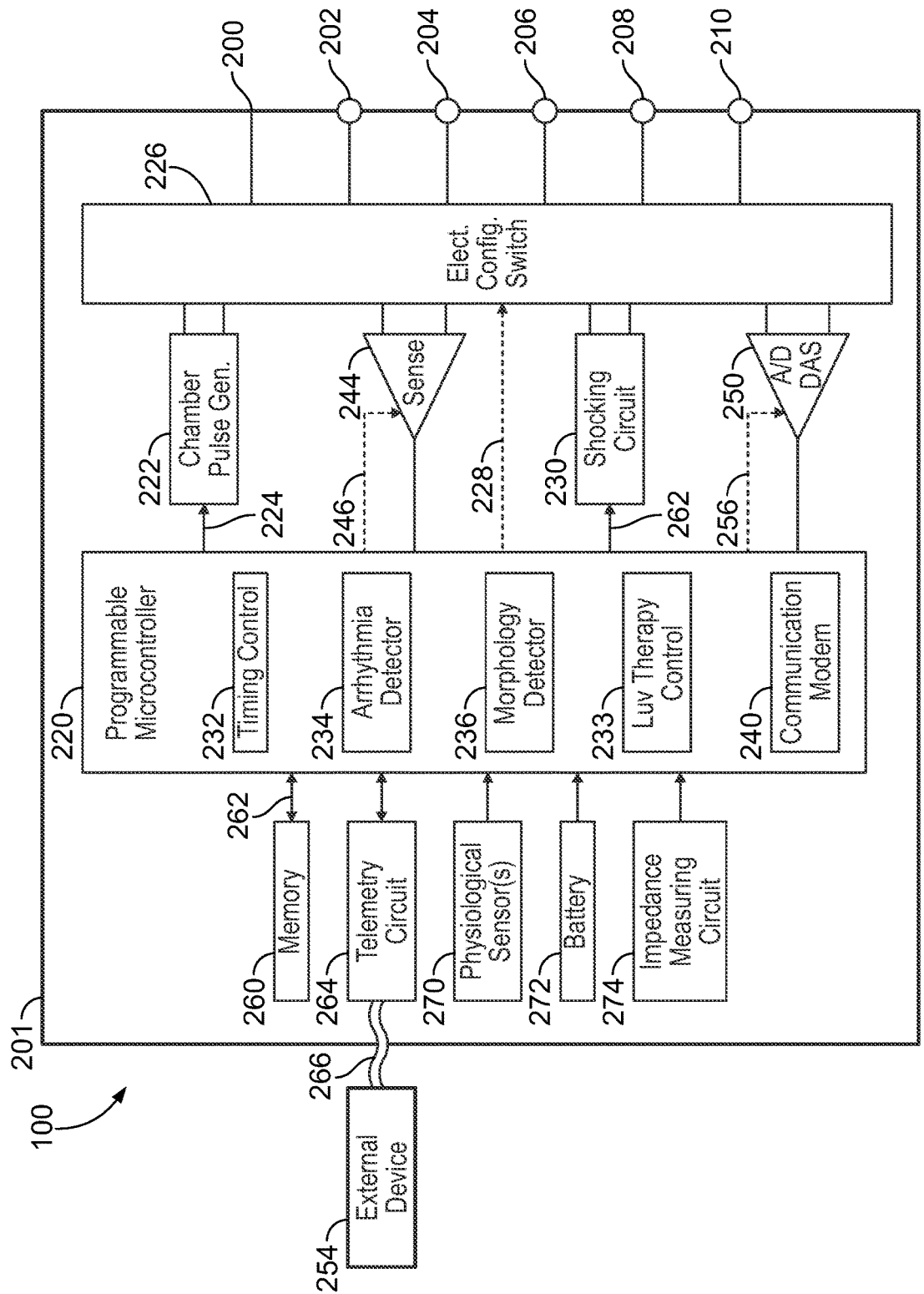
FIG. 2 shows a block diagram of an exemplary IMD that is implanted into the patient as part of the implantable cardiac system in accordance with embodiments herein.

To sense left atrial and ventricular cardiac signals and to provide left chamber pacing therapy, IMD 100 is coupled to a multi-pole LV lead 124 designed for placement in the "CS region" via the CS OS for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 124 is designed to receive atrial and ventricular cardiac signals and to deliver left ventricular pacing therapy using a set of four left ventricular electrodes $126_1$, $126_2$, $126_3$, and $126_4$ (thereby providing a quadrupole lead), left atrial pacing therapy using at least a left atrial ring electrode 127, and shocking therapy using at least a left atrial coil electrode 128 implanted on or near the left atrium. In other examples, more or fewer LV electrodes are provided. Although only three leads are shown, it should be understood that additional leads (with one or more pacing, sensing and/or shocking electrodes) might be used and/or additional electrodes might be provided on the leads already shown, such as additional electrodes on the RV lead. In this manner, electrodes are configured to be located proximate to an atrial (A) site, left ventricular (LV) site and right ventricular (RV) site of the heart FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing, and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing. As described herein, the IMD 100 is configured to provide LUV pacing therapy without pacing the RV.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber; a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the IMD 100 may include multiple pulse generators, similar to pulse generator 222, where each pulse generator is coupled to one or more electrodes and controlled by the microcontroller 220 to deliver select stimulus pulse(s) to the corresponding one or more electrodes.

The IMD 100 includes sensing circuitry 230 selectively coupled to one or more electrodes that perform sensing operations, through the switch 226 to detect the presence of cardiac activity in the right chambers of the heart. The sensing circuitry 230 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 100 to sense low amplitude signal characteristics of atrial fibrillation. The sensing circuitry 230 is configured to define an atrial sensing channel and an RV sensing channel where signals are received from each individual channel by the sensing circuitry 230. Switch 226 determines the sensing polarity of the cardiac signal by selectively closing the appropriate switches. In this way, the clinician may program the sensing polarity independent of the stimulation polarity.

The output of the sensing circuitry 230 is connected to the microcontroller 220 which, in turn, triggers or inhibits the pulse generator 222 in response to the absence or presence of cardiac activity. The sensing circuitry 230 receives a control signal 231 from the microcontroller 220 for purposes of controlling the gain, threshold, polarization charge removal circuitry (not shown), and the timing of any blocking circuitry (not shown) coupled to the inputs of the sensing circuitry.

In the example of FIG. 2, sensing circuitry 230 with a single sensing circuit is illustrated. Optionally, the IMD 100 may include multiple sensing circuits, similar to sensing circuitry 230, where each sensing circuit is coupled to one or more electrodes and controlled by the microcontroller 220 to sense electrical activity detected at the corresponding one or more electrodes. The sensing circuitry 230 may operate in a unipolar sensing configuration or in a bipolar sensing configuration.

Microcontroller 220 is illustrated to include timing control circuitry 232 to control the timing of the stimulation pulses (e.g., pacing rate, atrio-ventricular conduction ($AR_{RV}$) delay or interval, ventricular (V-V) conduction ($R_{LV}$-$R_{RV}$) delay or interval, etc.). In connection with embodiments herein, the timing control circuitry 232 is used to manage the timing of refractory periods, and blanking intervals associated with the refractory periods. Microcontroller 220 also has an arrhythmia detector 234 for detecting arrhythmia conditions and a morphology detector 236 to review and analyze one or more features of the morphology of cardiac signals.

The microcontroller 220 includes LUV therapy control circuitry 233 to implement the processes described herein for controlling an LV univentricular pacing therapy. The LUV therapy control circuitry 233 determines the $AR_{RV}$ (AV) conduction interval and $R_{LV}$-$R_{RV}$ (VV) conduction interval, and sets a ventricular refractory period (VRP) based on a comparison of the AV conduction interval and VV conduction interval. The VRP includes an offset, and the LUV therapy control circuitry 233 blanks signals over an RV sensing channel during the determined VRP to manage the LUV pacing therapy.

The LUV therapy control circuitry 233 obtains CA signals over the RV sensing channel of the sensing circuitry 230, the AV conduction interval determined based on a time between an atrial paced event and a first RV sensed event. The LUV therapy control circuitry 233 also deliverers an LV paced event at a LV site to obtain CA signals over the RV sensing channel of the sensing circuitry 230 and identify the time between the LV paced event and the RV sensed event to provide the VV conduction interval. The LUV therapy control circuitry 233, optionally, does not obtain signals at the LV site. The LUV therapy control circuitry 233 also identifies a longer one of the AV conduction interval and the VV conduction interval and sets the VRP based on the longer of the AV and VV conduction intervals.

The IMD 100 is further equipped with a communication modem (modulator/demodulator) 240 to enable wireless communication with other devices, implanted devices, and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 further includes an analog-to-digital (ND) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The memory 260 is configured to store the VRP set by the LUV therapy control circuitry 233 based on the AV conduction interval and VV conduction interval. In addition, the sensing circuitry 230 continues determining AV conduction intervals and VV conduction intervals to determine when a RV event is not a PVC. In each instance, the microcontroller adds a count to a stored false PVC count. Once the false PVC count reaches and/or exceeds a threshold amount, such as three counts, a LV paced event is delivered to redetermine the VRP. In one example, the threshold amount may be determined based on a time dependent basis such that the threshold amount must be reached during a determined period. In an example, the determined period could be a day, such that if three false PVCs occur in a twenty-four hour period, the VRP is redetermined.

A battery 272 provides operating power to all of the components in the IMD 100. The battery 272 is capable of operating at low current drains for long periods of time, and is capable of providing high-current pulses (for capacitor charging) when the patient requires a shock pulse (e.g., in excess of 2A, at voltages above 2 V, for periods of 10 seconds or more). The battery 272 also desirably has a predictable discharge characteristic so that elective replacement time can be detected.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart 112 through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Figure 3:
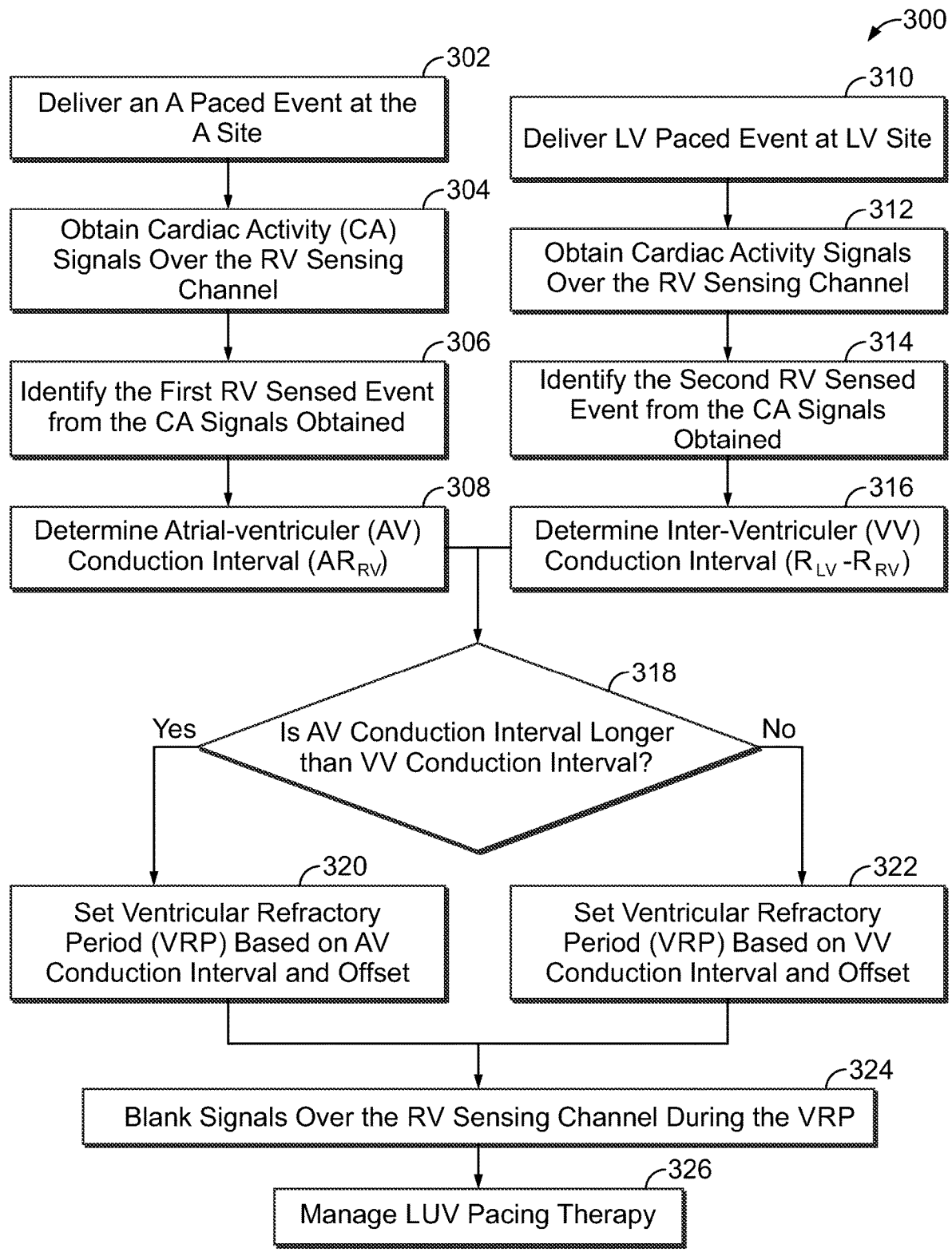
FIG. 3 illustrates a flow block diagram of a method for controlling left univentricular (LUV) pacing therapy using an IMD in accordance with embodiments herein.

FIG. 3 illustrates a method for controlling left univentricular (LUV) pacing therapy using an implantable medical device (IMD). In one embodiment, the IMD of FIGS. 1 and 2 accomplishes the method. In another embodiment, the method is accomplished by an IMD that lacks, or does not include, RV pacing, and is providing only LV pacing.

At 302, an IMD delivers an atrial (A) paced event at an A site. The A site may include any location within the right atrial. Alternatively, the IMD senses an A event. To this end, any of the step 304-308 may be applied to an IMD sensing an A event. At 304, one or more processors obtain electrical cardiac activity (CA) signals over a right ventricle (RV) sensing channel. In one embodiment, the RV sensing channel is defined by sensing circuitry that monitors electrical activity of the heart. In one example, the sensing circuitry is the sensing circuitry described in relation to FIG. 2. The RV sensing channel extends along an RV sensing vector through a desired portion of the right ventricle. In this manner, the paced event at the A site is sensed at a RV site.

At 306, the one or more processors analyze the cardiac activity signals to identify a RV sensed event that occurred in response to the A paced event. For the method 300, the RV sensed event is a first RV sensed event that is associated with the IMD pacing, whereas concurrently, an LV paced event is also delivered, providing a second RV sensed event (e.g. 310-316). Optionally, the RV sensed event identified from the LV paced event may be considered a first RV sensed event, while the RV sensed event identified from the delivered A paced event may be considered the second RV sensed event. In one example, the delay from the RA paced event and RV sensed event (AV delay) is measured with no LV pacing. In one example, the RA paced event is approximately 10 bpm higher than the intrinsic heart rate. In one example, the AV delay is approximately 50 ms while the sensed AV delay is approximately 25 ms.

At 308, the one or more processors determine an atrioventricle (AV) conduction interval ($AR_{RV}$) between the A paced event and the RV sensed event RAp/RAs-RVs. Additionally or alternatively, the operation at 306 may be implemented based on an intrinsic atrial event. For example, the one or more processors may sense an atrial intrinsic event over the atrial sensing channel and record a timestamp at which the atrial event occurred. Thereafter, the one or more processors analyze the CA signals sensed over the RV sensing channel for a corresponding subsequent RV sensed event.

Subsequent to the operations at 302 to 308, the one or more processors manage the operations at 310 to 316. For example, the operations at 302 to 308 may be performed during one beat and the operations at 310 to 316 may be performed during the next (or a later) beat. Optionally, the operations at 302 to 308 may be repeated for a first group of beats to determine the $AV_{RV}$ based on an ensemble of beats. Thereafter, the operations at 310 to 316 may be repeated for a second group of beats to determine the VV conduction internal $R_{LV}$-$R_{RV}$ based on an ensemble of beats.

At 310, the one or more processors deliver a left ventricle (LV) paced event at one or more LV sites. At 312, the one or more processors obtain CA signals over the RV sensing channel as described above in relation to 304.

At 314, the one or more processors identify the second RV sensed event from the CA signals in connection with the LV paced event. The sensing circuitry does not obtain signals at the LV site, and only signals from the RV sensing channel are utilized. Also, as indicated above, the RV sensed event may be considered the first RV sensed event or second RV sensed event. The delay from LV paced event to the RV sensed event are measured (LVp-RVs) at the shortest possible paced/sensed AV delay to ensure sensing in the RV is due to the LV pacing wave front.

At 316, the one or more processors determine the interventricular (VV) conduction interval ($R_{LV}$-$R_{RV}$). Additionally or alternatively, the operation at 306 may be implemented based on an intrinsic ventricle event. For example, the one or more processors may sense a ventricle intrinsic event over the ventricle sensing channel and record a timestamp at which the ventricle event occurred. Thereafter, the one or more processors analyze the CA signals sensed over the RV sensing channel for a corresponding subsequent RV sensed event.

At 318, the one or more processors determine whether the AV conduction interval is longer than the VV conduction interval. In one embodiment, the one or more processors compare lengths of the VV conduction interval and AV conduction interval to identify which is longer. If the AV conduction interval is longer, flow moves to 320. At 320, the one or more processors add a predetermined offset to the determined AV conduction interval to set a ventricular refractory period (VRP). The predetermined offset is a determined amount of time to account for error and/or randomness, and in one example may be between 10 ms to 50 ms. In other embodiments, the predetermined offset is greater than 50 ms. The predetermined offset may be pre-programmed by a clinician or automatically determined by the IMD. For example, the predetermined offset may be set by a clinician to a desired number milliseconds or percentage of the VV or AV conduction interval. When the predetermined offset is determined automatically, the IMD may define the predetermined offset based on the function of the longer of the VV or AV conduction intervals. For example, the IMD may define the predetermined offset to be 10% of the AV or VV conduction interval.

If the VV conduction interval is longer, flow moves to 322. At 322 the one or more processors add the predetermined offset to the determined VV conduction interval to set the VRP. Again, the predetermined offset may be determined such that the predetermined offset is the same, whether the AV conduction interval is longer or the VV conduction interval is longer. At the time the VRP is set, the one or more processors may optionally start a counter set at zero to make determination regarding when to update or change the VRP as will be detailed in relation to FIG. 4. In this manner, calibration may be provided for the system.

At 324, whether the AV conduction interval was longer, or the VV conduction interval, the one or more processors set a blanking interval for the RV sensing channel to blank signals over the RV sensing channel during the VRP. The VRP corresponds to a blanking interval, which is an interval of time during which signals that occur over the RV sensing channel are ignored. In one example, the RV sensing channel stops collecting CA signals during the blanking interval. Alternatively, the RV sensing channel receiving CA signals during the blanking interval, but does not pass the CA signals to the microprocessor during the blanking interval. In yet another embodiment, the RV sensing channel receives signals, and communicates the signals to the one or more processors; however, the one or more processors do not use such signals in algorithms, functions, equations, etc. used to determine the presence of an event.

In accordance with new and unique aspects herein, methods and systems reduce ventricle oversensing when using LV only pacing by blanking the signal during the VRP interval. Specifically, double-counting of ventricle events in the RV lead is reduced compared to systems not using this methodology. Additionally, the VRP is ensured to be more accurate, ensuring improved functionality of the system.

At 326, the IMD manages LUV pacing therapy using the VRP, and blanking the signals during the VRP. In this manner, LV only pacing may be utilized without oversensing, which improves accuracy, improves therapy efficacy, and reduces power usage by the IMD. Specifically, LUV pacing therapy is not based on signals sensed in the LV, or chamber where pacing is occurring.

Figure 4:
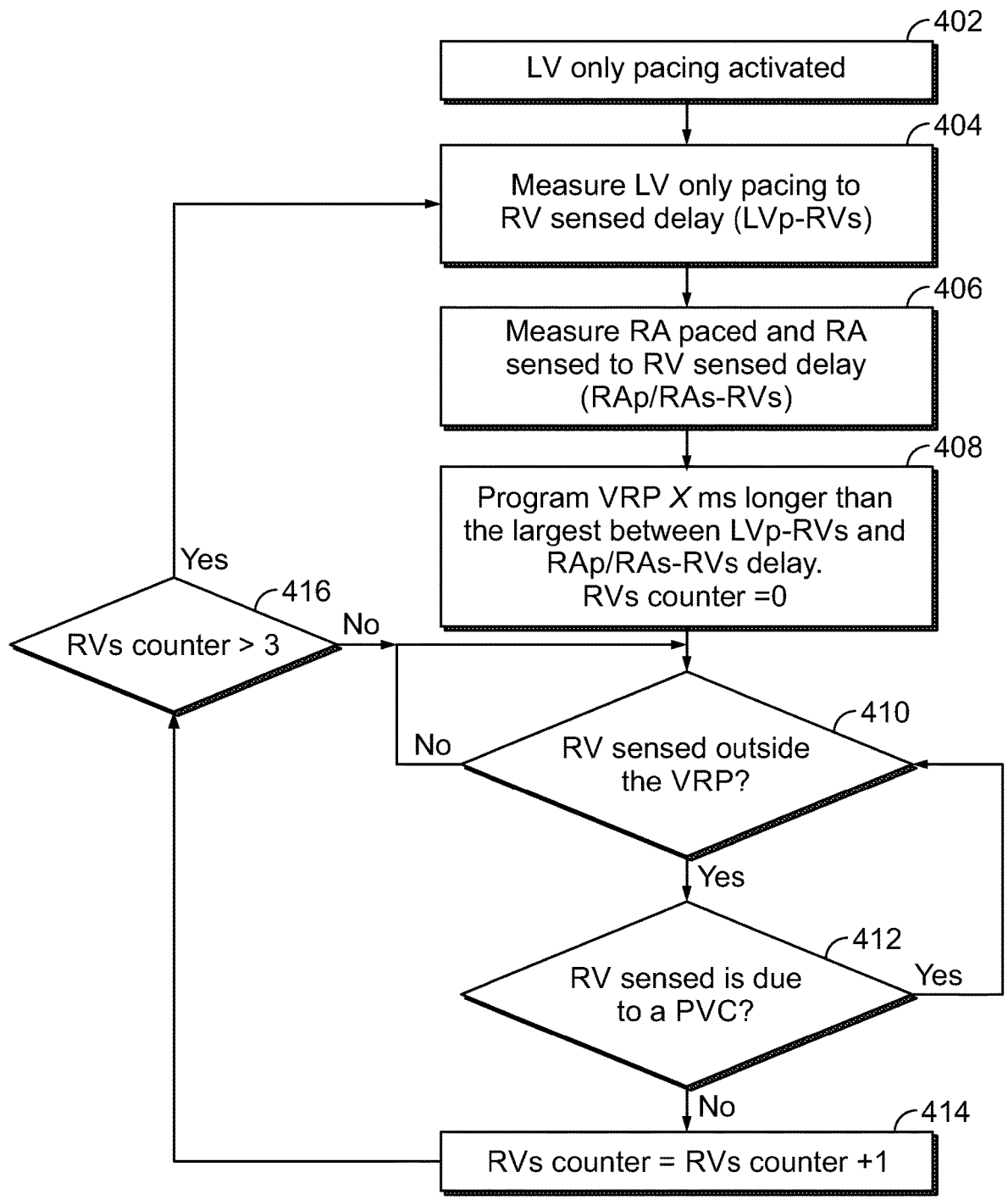
FIG. 4 illustrates a flow block diagram of a method of automatically updating a ventricular refractory period (VRP) in accordance with embodiments herein.

FIG. 4 illustrates a method for automatically updating a ventricular refractory period (VRP) in accordance with embodiments herein. At 402, one or more processors of an implantable medical device implement LV only pacing.

At 404, an LV paced event is delivered at one or more LV sites and the one or more processors obtain CA signals over the RV sensing channel. The one or more processors analyze the CA signals to identify an RV sensed event that occurred in response to the LV paced event. The one or more processors determine a VV conduction interval between the LV paced event and the RV sensed event.

At 406, an atrial paced event is delivered at an A site and the one or more processors obtain CA signals over the RV sensing channel. The one or more processors analyze the CA signals to identify an RV sensed event that occurred in response to the A paced event. The one or more processors determine an AV conduction interval between the atrial paced event on the RV sensed event. Additionally or alternatively, the operation at 406 may be implemented based on intrinsic atrial event. For example, the one or more processors may sense an atrial intrinsic event over the atrial sensing channel and record a timestamp at which the atrial event occurred. Thereafter, the one or more processors analyze the CA signals sensed over the RV sensing channel for a corresponding subsequent RV sensed event.

At 408, the one or more processors compare lengths of the VV conduction interval and AV conduction interval to identify which is longer. The one or more processors then utilize the longer of the VV conduction interval and AV conduction interval, and add thereto a predetermined offset, to obtain a ventricular refractory period (VRP) to be used in connection with the RV sensing channel. As described in relation to the method of FIG. 3, the predetermined offset may be preprogrammed by a clinician or automatically determined by the IMD.

At 410, the one or more processors initiate or continue in LUV therapy utilizing the new VRP to define a blanking interval during which signals are ignored when sensed over the RV sensing channel. At 410, the one or more processors determine whether an RV event is sensed over the RV sensing channel outside of the VRP. When no RV is sensed outside of the VRP, the process continues to monitor subsequent beats at 410. Once a beat is detected at 410 for which an RV event is sensed outside of the VRP, flow continues to 412.

At 412, the one or more processors apply a PVC detection process to determine whether the RV event that was sensed is due to a premature ventricular contraction (PVC). When the RV event is deemed to be due to a PVC, flow returns to 410. When the RV event is determined to not be due to a PVC, flow continues to 414. At 414, an RV counter is incremented. The RV counter maintains a count of the number of events that are sensed outside of the VRP.

At 416, the one or more processors determine whether the RV counter has exceeded a threshold. For example, the threshold may be set to three, five and the like. When the RV counter exceeds a threshold, flow returns to 404. Alternatively, when the RV counter does not exceed the threshold, flow returns to 410. In this manner, the system continuously records if a ventricle sensed event is detected just outside of the VRP. If an event is sensed, first it is verified if the origin is a PVC. If so, then system continues monitoring. If it is not a PVC, then the RVs counter is increased by 1 (RVs=RVs+1) so that the system may be updated, or continuously calibrated. In one example, after a determined amount of time, the counter may decrease by one to attempt to ensure recalibration only occurs when changes have occurred, and not due to a bad signal, or temporary monitoring malfunction.

Figure 5:
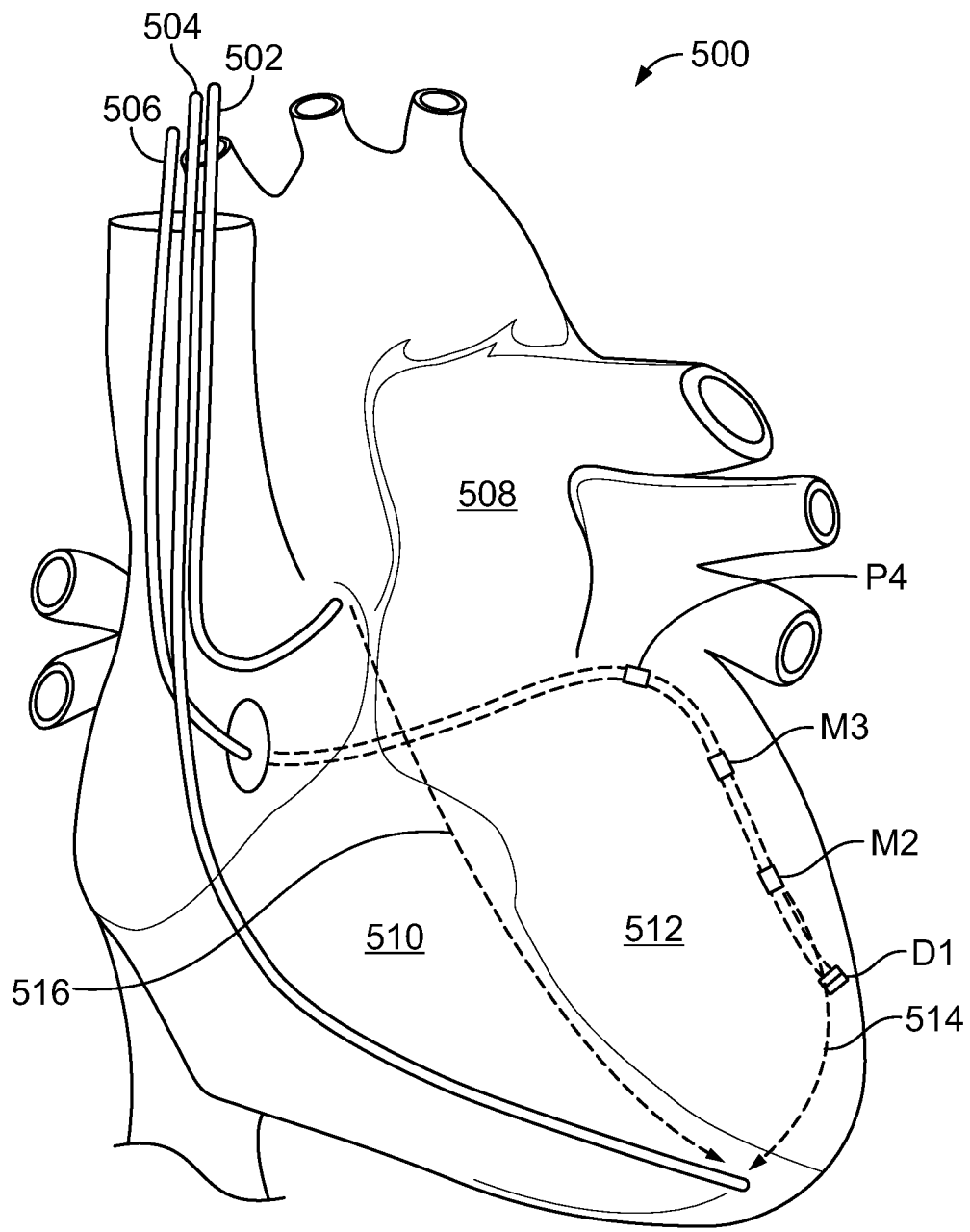
FIG. 5 illustrates an anatomical diagram of a heart in accordance with embodiments herein.

FIG. 5 illustrates an example anatomical diagram of the heart 500 in connection with determining VRP in accordance with embodiments herein. Specifically, the illustration shows leads 502, 504, 506 of an IMD utilized for cardiac resynchronization therapy. A first lead 502 is in the right atrium (RA) 508, a second lead 504 is in the right ventricle (RV) 510, and the third lead 506 is in the left ventricle (LV) 512. Using this arrangement, RA to RV sensed (either atrial sensed [RAs] or atrial paced [RAp]) and LV paced (LVp) to RVs delays are provided. Using the arrangement, the paced event and sensed event are in different chambers of the heart. The delay from LVp to the RVs is measured as LVp-RVs 514 at the minimum possible paced and sensed AV delay to ensure sensing in the RV 510 is due to the LV pacing wave front. The pacing may occur at any point P4, M3, M2, or D1 to the RV. In one example, the minimum possible AV delay is 50 ms while the minimum possible sensed AV delay is 25 ms. Meanwhile, the delay from the RA paced and RA sensed measurements is measured to the RV with no LV pacing. The measurement is RAp/RAs-RVs 516.

Figure 6:
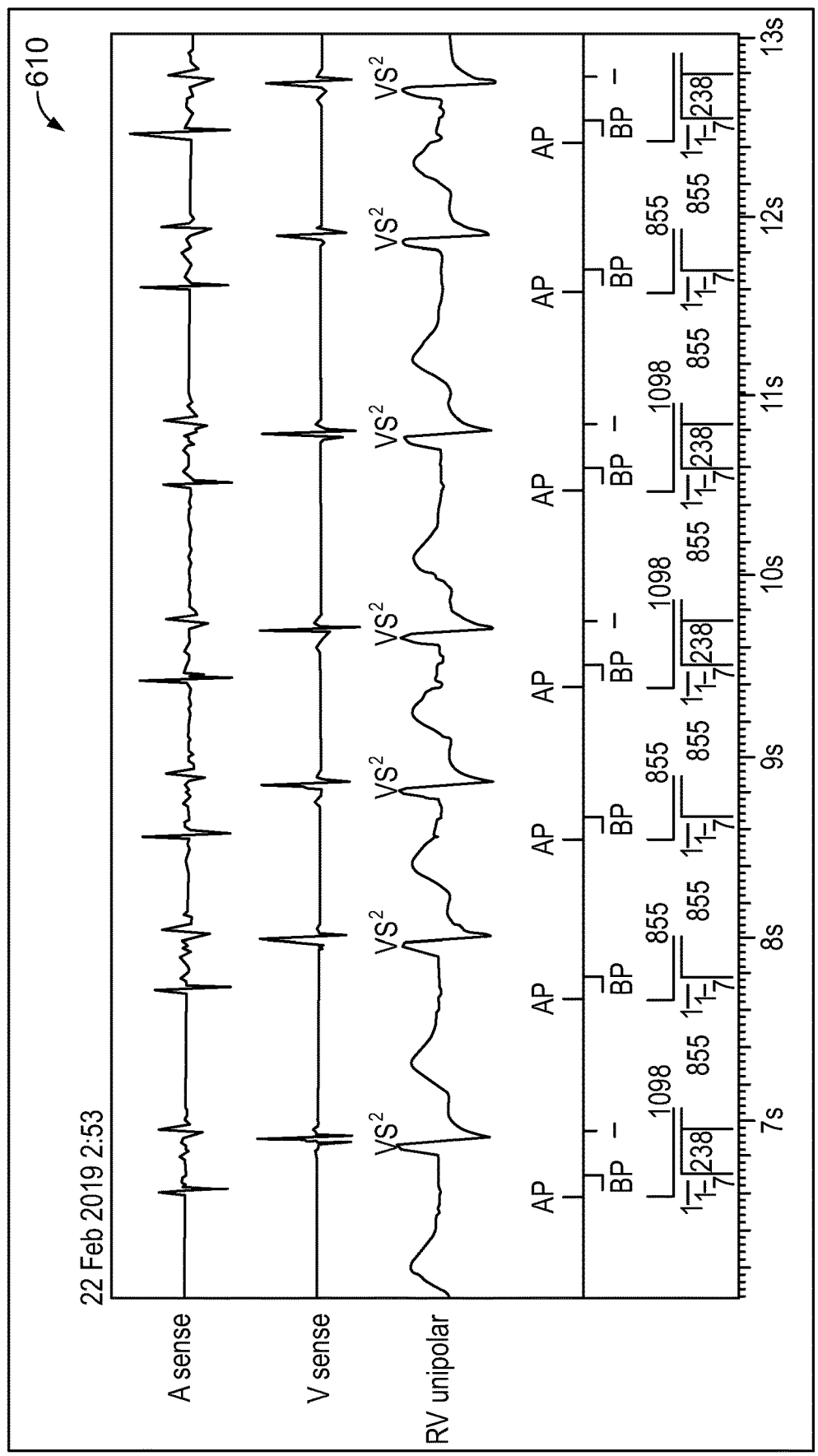
FIG. 6 illustrates a waveform sensed by an IMD in accordance with embodiments herein.

FIG. 6 shows a set of waveforms 610 that include an atrial event (e.g., A sense), a ventricle event (e.g. V sense), and a RV unipolar event (RV unipolar) where RV oversensing is provided such that blanking of a signal would be advantageous. In the example, only LV pacing is provided at 120 ms after A pacing, and the pacing wave front is being detected by the RV sensing detector. Using a blanking period during the period the oversensing is occurring prevents misdiagnosis. In particular, because only LV pacing is provided, such sensing cannot be as a result of RV pacing, and therefore can be blanked as a known over sense. Because the over sensed signal occurs at a time that sensing of LV is not expected, blanking does not have a negative effect.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system for controlling a left univentricular (LUV) pacing therapy using an implantable medical device (IMD), the system comprising:
   electrodes configured to be located proximate to a left ventricular (LV) site and a right ventricular (RV) site of the heart;
   a sensing circuitry configured to define an RV sensing channel;
   memory to store program instructions;

one or more processors configured to implement the program instructions to:
  determine an inter-ventricular (VV) conduction interval ($R_{LV}$-$R_{RV}$) between a paced event at the LV site and an RV sensed event at the RV site;
  set a ventricular refractory period (VRP) based on the VV conduction interval and a predetermined offset;
  blank signals over the RV sensing channel during the VRP; and
  manage the LUV pacing therapy based on the signals sensed over the RV sensing channel outside of the VRP, wherein the LUV pacing therapy lacks pacing in the RV.

2. The system of claim 1, wherein the LUV pacing therapy is not based on signals sensed in the LV.

3. The system of claim 1, wherein the one or more processors are further configured to deliver an LV paced event at the LV site, obtain cardiac activity (CA) signals over the RV sensing channel and identify the RV sensed event from the CA signals obtained over the RV sensing channel, the VV conduction interval determined based on the time between the LV paced event and the second RV sensed event.

4. The system of claim 1, wherein the sensing circuitry does not obtain signals at the LV site.

5. The system of claim 1, further comprising:
  an electrode configured to be located proximate to an atrial (A) site,
  the sensing circuitry further configured to define an atrial sensing channel;
  the one or more processors further configured to implement the program instructions to:
    determine an atrial-ventricular (AV) conduction interval ($AR_{RV}$) between the A site and a first RV sensed event at the RV site; and
    set the VRP based on the AV conduction interval and the predetermined offset.

6. The system of claim 5, wherein the one or more processors are further configured to identify a longer one of the AV conduction interval and the VV conduction interval, the VRP set based on the longer one of the AV and VV conduction intervals.

7. The system of claim 1, wherein the VRP defines a blanking interval during which signals, that occur over the RV sensing channel, are ignored.

8. A computer implemented method for controlling a left univentricular (LUV) pacing therapy using an implantable medical device (IMD), the method comprising:
  determining an inter-ventricular (VV) conduction interval ($R_{LV}$-$R_{RV}$) between a paced event at a left ventricular (LV) site and a RV sensed event at a right ventricular (RV) site;
  setting a ventricular refractory period (VRP) based on the VV conduction interval and a predetermined offset;
  blanking signals over a RV sensing channel during the VRP; and
  managing the LUV pacing therapy based on the signals sensed over the RV sensing channel outside of the VRP, wherein the LUV pacing therapy lacks pacing in the RV.

9. The computer implemented method of claim 8, wherein the LUV pacing therapy is not based on signals sensed in the LV.

10. The computer implemented method of claim 8, further comprising delivering an LV paced event at the LV site, obtaining cardiac activity (CA) signals over the RV sensing channel and identifying the second RV sensed event from the CA signals obtained over the RV sensing channel, the VV conduction interval determined based on the time between the LV paced event and the second RV sensed event.

11. The computer implemented method of claim 8, wherein the sensing circuitry does not obtain signals at the LV site.

12. The computer implemented method of claim 8, further comprising:
  delivering an A paced event at the A site, obtaining cardiac activity (CA) signals over the RV sensing channel, and identifying a second RV sensed event from the CA signals obtained over the RV sensing channel; and
  determining an atrial-ventricular (AV) conduction interval ($AR_{RV}$) based on a time between the A paced event and the second RV sensed event.

13. The computer implemented method of claim 12, further comprising identifying a longer one of the AV conduction interval and the VV conduction interval, the VRP set based on the longer one of the AV and VV conduction intervals.

14. The computer implemented method of claim 8, wherein the VRP defines a blanking interval during which signals, that occur over the RV sensing channel, are ignored.

15. A system for controlling a left univentricular (LUV) pacing therapy using an implantable medical device (IMD), the system comprising:
  electrodes configured to be located proximate a left ventricular (LV) site and a right ventricular (RV) site of the heart;
  sensing circuitry configured to define an RV sensing channel;
  memory to store program instructions;
  one or more processors configured to implement the program instructions to:
    determine an inter-ventricular (VV) conduction interval ($R_{LV}$-$R_{RV}$) between a paced event at the LV site and a first RV sensed event at the RV site;
    set a ventricular refractory period (VRP) based on the VV conduction interval and a predetermined offset;
    blank signals over the RV sensing channel during the VRP;
    manage the LUV pacing therapy based on the signals sensed over the RV sensing channel outside of the VRP, wherein the LUV pacing therapy lacks pacing in the RV;
    when a second RV event is sensed outside of the VRP, apply a premature ventricular contraction (PVC) detection to determine whether the second RV event is due to a PVC; and
    increment an RV counter when the second RV event is determined to not be a PVC.

16. The system of claim 15, wherein the LUV pacing therapy is not based on signals sensed in the LV.

17. The system of claim 15, wherein the one or more processors are further configured to deliver an LV paced event at the LV site, obtain cardiac activity (CA) signals over the RV sensing channel and identifying the second RV sensed event from the CA signals obtained over the RV sensing channel, the VV conduction interval determined based on the time between the LV paced event and the second RV sensed event.

18. The system of claim 15, wherein the sensing circuitry does not obtain signals at the LV site.

19. The system of claim 15, further comprising:
  an electrode configured to be located proximate to an atrial (A) site, the sensing circuitry further configured to define an atrial sensing channel;

the one or more processors further configured to:
   determine an atrial-ventricular (AV) conduction interval ($AR_{RV}$) between the A site and a third RV sensed event at the RV site.

20. The system of claim 19, wherein the one or more processors are further configured to identify a longer one of the AV conduction interval and the VV conduction interval, the VRP set based on the longer one of the AV and WV conduction intervals.

* * * * *